United States Patent
Martinez-Gomez

(10) Patent No.: US 11,812,750 B2
(45) Date of Patent: Nov. 14, 2023

(54) RARE EARTH DEPENDENT PLANT PROBIOTIC COMPOSITIONS AND METHODS OF USE

(71) Applicant: BOARD OF TRUSTEES OF MICHIGAN STATE UNIVERSITY, East Lansing, MI (US)

(72) Inventor: Norma Cecilia Martinez-Gomez, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 506 days.

(21) Appl. No.: 15/733,132

(22) PCT Filed: Nov. 21, 2018

(86) PCT No.: PCT/US2018/062251
§ 371 (c)(1),
(2) Date: May 22, 2020

(87) PCT Pub. No.: WO2019/104171
PCT Pub. Date: May 31, 2019

(65) Prior Publication Data
US 2020/0367506 A1    Nov. 26, 2020

Related U.S. Application Data

(60) Provisional application No. 62/589,649, filed on Nov. 22, 2017.

(51) Int. Cl.
*A01N 63/20* (2020.01)
*A01C 1/06* (2006.01)
(Continued)

(52) U.S. Cl.
CPC ............ *A01N 63/20* (2020.01); *A01C 1/06* (2013.01); *A01C 23/047* (2013.01); *A01G 7/06* (2013.01);
(Continued)

(58) Field of Classification Search
CPC ............................. A01N 63/20; A01N 59/16
See application file for complete search history.

(56) References Cited

U.S. PATENT DOCUMENTS

| | | | |
|---|---|---|---|
| 9,181,541 B2 | 11/2015 | Bogosian | |
| 2016/0073641 A1 | 3/2016 | Allen et al. | |
| 2017/0311602 A1* | 11/2017 | Dutzmann | ............ A01N 25/00 |

FOREIGN PATENT DOCUMENTS

| | | |
|---|---|---|
| CN | 101905993 A | 12/2010 |
| CN | 106233994 A | 12/2016 |
| WO | 2017027821 A1 | 2/2017 |

OTHER PUBLICATIONS

Abanda-Nkpwatt et al. (Molecular interaction between Methylobacterium extoquens and seedlings: growth promotion, methanol consumption, and localization of the methanol emission site, Journal of Experimental Botany, vol. 57, No. 15, pp. 4025-4032, 2006) (Year: 2006).*

(Continued)

*Primary Examiner* — Johann R Richter
*Assistant Examiner* — Danielle Sullivan
(74) *Attorney, Agent, or Firm* — McKee, Voorhees & Sease, PLC

(57) ABSTRACT

The present invention provides probiotic compositions for promoting plant growth. The compositions include bacterial cultures of phyllobacteria and rhizobacteria isolated from media supplemented with rare earth elements. Applicants have found that such bacteria act synergistically with rare earth elements to enhance plant growth. Inoculums of the plant growth promoting bacteria for application to plants, (Continued)

plant seeds, or plant growth media are provided. Also provided are methods for stimulating plant growth by applying the bacterial cultures and inoculums.

42 Claims, 11 Drawing Sheets

(51) Int. Cl.
    *A01C 23/04*     (2006.01)
    *A01G 7/06*     (2006.01)
    *A01M 7/00*     (2006.01)
    *A01M 21/04*     (2006.01)
    *A01N 31/08*     (2006.01)
    *A01N 59/16*     (2006.01)

(52) U.S. Cl.
    CPC ............ *A01M 7/00* (2013.01); *A01M 21/043* (2013.01); *A01N 31/08* (2013.01); *A01N 59/16* (2013.01)

(56) References Cited

OTHER PUBLICATIONS

Vu et al., "Lanthanide-Dependent Regulation of Methanol Oxidation Systems in Methylobacterium extorquens AM1 and Their Contribution to Methanol Growth", Journal of Bacteriology, vol. 198, No. 8, pp. 1250-1259, Apr. 2016.

\* cited by examiner

RARE EARTH DEPENDENT PLANT PROBIOTIC COMPOSITIONS AND METHODS OF USE

CROSS-REFERENCE TO RELATED APPLICATIONS

This application claims priority under 35 U.S.C. § 119 to provisional application Ser. No. 62/589,649 filed Nov. 22, 2017, herein incorporated by reference in its entirety.

FIELD OF THE INVENTION

The present invention generally relates to specific bacterial cultures of plant growth-promoting bacteria, compositions and inoculums comprising the same. The invention is also directed to plant seeds coated with the compositions or inoculums, kits comprising the same and methods for stimulating plant growth by using the same.

BACKGROUND OF THE INVENTION

Microbes affect and are affected by their hosts in a manner that depends upon environmental conditions. Plant metabolism is a classic case of this; many processes can only be fully understood in the context of the interaction of plants with diverse organisms. In particular, bacterial communities in the rhizosphere and phyllosphere can influence the growth and resistance of their hosts to biotic and abiotic stresses. Despite our limited knowledge of the traits and plant-microbe interactions by which bacteria promotes plant growth, a growing number of bacteria are applied to seeds and plants in commercial agriculture. Application of biostimulants such as agrochemicals have been successful in enhancing plant yields but they are costly, both financially and environmentally. Further, the biochemical mechanisms in which agrochemicals enhance plant productivity are not completely understood.

Rare earth element (REE)-enriched fertilizers have been used broadly since 1980, starting in China and later in Canada, the United States, Australia, and numerous countries in Europe. The word "rare" in REE is misleading, as these metals are commonly found in soils worldwide. However, unlike many other metals, REE are highly insoluble and rarely found in pure form. Commercial fertilizers contain a mix of REE, primarily lanthanum (La), cerium (Ce), praseodymium (Pr), and neodymium (Nd) in their nitrate, oxide, or chloride forms. Although there has not been any proposed biochemical mechanism for how REE affect plant growth, it has been reported that REE accelerate soybean rhizogenesis, increase the amount of roots by 35%, and root length by 10%, improve nitrogen utilization including its absorption, and enhance nitrate reductase activity in leaves. Other beneficial effects linked to the addition of REE include increased resistance to drought, cold, and heavy metals, but the physiological basis of these effects are not understood. Repetitive spraying of crops results in accumulation of REE, predominantly in the roots and the leaves of the plant, and this has a toxic effect. Therefore, accumulation of these elements in plants or soils is of great concern. Although REE have been used for decades in agriculture, there is no mechanism to explain growth stimulation (or toxicity), and thus no principles to guide their application.

SUMMARY OF THE INVENTION

In one embodiment the invention is directed to a bacterial culture of one or more phyllobacteria strains grown on media supplemented with rare earth elements (REE) (such as lanthanum, cerium, praseodymium and/or neodymium in their nitrate, oxide or chloride forms). In one embodiment the bacteria is preferably a methylobacterium. In an embodiment the methylobacterium is a strain of *M. extorquens*, isolated and purified from the culture to create a biologically pure culture of one or more such strains. Also provided are biologically pure bacterial cultures wherein bacteria in the culture are mutants of any of the foregoing strains comprising one or more mutations which retain the ability to promote plant growth. In an embodiment the REE are at a concentration normally found in the earth's crust (as low as 200 nM).

The present invention is also directed to an inoculum for application to plants, plant seeds, or a plant growth medium, wherein the inoculum comprises an effective amount of the aforementioned bacterial culture preferably in combination with methanol.

In another embodiment the invention includes an inoculum comprising rhizobacteria and or phyllobacteria and REEs, preferably lanthanides. Applicants have found that when lanthanides are co-inoculated with such bacteria, the bacteria exhibit increased production of organic acids and hormones. When introduced to plants these bacteria induce increased plant yield and growth. In an embodiment the rhizobacterium is *B. diazoefficiens*. In an embodiment the phyllobacteria is *M. extorquens*.

In another embodiment the invention is directed to an inoculum comprising an effective amount of a bacterial culture and an agriculturally acceptable carrier.

Yet another aspect of the present invention is a method for stimulating plant growth by applying the bacterial culture or the inoculum as disclosed herein to a plant, plant seed, or plant growth medium.

The present invention also provides a method for stimulating plant growth by applying at least one bacterial culture or at least one inoculum to a plant or plant seed in the plant growth medium, or to the plant growth medium, wherein the at least one bacterial culture or at least one inoculum is capable of stimulating plant growth.

Another aspect of the present invention is a provision of a plant seed coated with the inoculum or with the bacterial culture disclosed herein.

Yet another aspect of the present invention is a kit for stimulating plant growth comprising an inoculum disclosed herein and instructions for applying the inoculum to plants, plant seeds, or a plant growth medium.

The present invention also provides a method for isolating methylotrophic bacteria from a plant by obtaining a sample from a plant and inoculating rare earth element enriched media with the sample.

Other objects and features will be in part apparent and in part pointed out hereinafter. While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

FIG. 5A shows growth of an mxaF mutant strain in methanol minimal medium with 2 μM REE. FIG. 5B shows growth of mxaF mutant strain in methanol medium containing 20 μM $Ca^{2+}$ without and with increasing concentrations of $La^{3+}$.

DETAILED DESCRIPTION OF THE INVENTION

Figure 1:
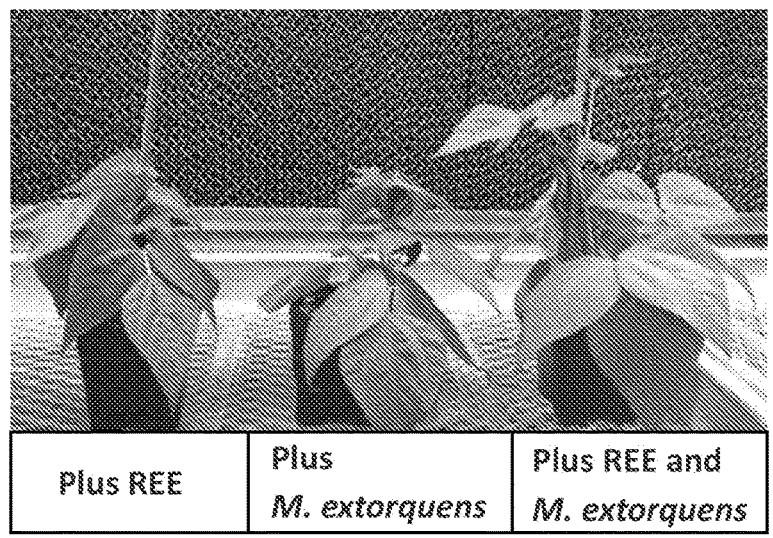
FIG. 1 shows methylotrophs synergistically enhance REE effect on plant growth.

As used herein the term "biologically pure bacterial culture" refers to a culture of bacteria containing no other bacterial species in quantities sufficient to interfere with the replication of the culture or be detected by normal bacteriological techniques. Stated another way, it is a culture wherein virtually all of the bacterial cells present are of the selected strain.

In addition to one or more bacterial cultures as described in the foregoing sections, an inoculum of the present invention also comprises an agriculturally acceptable carrier. The carrier can include a dispersant, a surfactant, an additive, water, a thickener, an anti-caking agent, residue breakdown, a composting formulation, a granular application, diatomaceous earth, an oil, a coloring agent, a stabilizer, a preservative, a polymer, a coating, or a combination thereof. One of ordinary skill in the art can readily determine the appropriate carrier to be used taking into consideration factors such as a particular bacterial strain, plant to which the inoculum is to be applied, type of soil, climate conditions, whether the inoculum is in liquid, solid or powder form, and the like.

The additive can comprise an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutant dioate, a benzene acetonitrile derivative, a proteinaceous material, or a combination thereof.

The proteinaceous material can include a milk product, wheat flour, soybean meal, blood, albumin, gelatin, or a combination thereof.

The thickener can comprise a long chain alkylsulfonate of polyethylene glycol, polyoxyethylene oleate, or a combination thereof.

The surfactant can contain a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof.

The anti-caking agent can include a sodium salt such as a sodium sulfite, a sodium sulfate, a sodium salt of monomethyl naphthalene sulfonate, a sodium salt of dimethyl naphthalene sulfonate, or a combination thereof; or a calcium salt such as calcium carbonate, diatomaceous earth, or a combination thereof.

Any agriculturally acceptable carrier can be used. Such carriers include, but are not limited to, vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

Inoculants can be prepared as solid, liquid or powdered formulations as is known in the art. The inoculum of the present invention can be formulated as a seed coating formulation, a liquid formulation for application to plants or to a plant growth medium, or a solid formulation for application to plants or to a plant growth medium.

When the inoculum is prepared as a liquid formulation for application to plants or to a plant growth medium, it can be prepared in a concentrated formulation or a working form formulation. In some instances, the seed coating formulation of the present invention is an aqueous or oil-based solution for application to seeds.

When the inoculum of the present invention is prepared as a solid formulation for application to plants or to a plant growth medium, it can be prepared as a granular formulation or a powder agent. The seed coating formulation can be a powder or granular formulation for application to seeds.

The inoculum can further include an agrochemical such as a fertilizer, a micronutrient fertilizer material, an insecticide, a herbicide, a plant growth amendment, a fungicide, a molluscicide, an algicide, a bacterial inoculant, a fungal inoculant, or a combination thereof. In some instances, the fertilizer is a liquid fertilizer. The agrochemical can either be applied to a plant growth medium or to plants and/or seeds. Liquid fertilizer can include, without limitation, ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$, $2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, or a combination thereof.

The micronutrient fertilizer material can comprise boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof.

The insecticide can include an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

The herbicide can comprise a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivative, oxadiazolinone, a phosphate, a phthalate, a picolinic acid compound, a triazine, a triazole, a uracil, a urea derivative, endothall, sodium chloride, or a combination thereof.

The fungicide can comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

All of the bacterial cultures and inoculums of the present invention can be used in methods for stimulating plant growth. Such methods include applying the foregoing cultures and inoculums to a plant, plant seed, or plant growth medium in order to stimulate growth of the plant. Techniques for applying inoculants to plants are known in the art, including appropriate modes of administration, frequency of administration, dosages, and the like. The inoculant can be applied to the soil prior to, contemporaneously with, or after sowing seeds, after planting, or after plants have emerged from the ground. The inoculant can also be applied to seeds themselves prior to or at the time of planting (e.g., packaged seed may be sold with the inoculant already applied). The inoculant can also be applied to the plant after it has emerged from the ground, or to the leaves, stems, roots, or other parts of the plant.

The method for stimulating plant growth can include applying a substance such as glycerol, pyruvate, yeast extract, or polyol to the plant growth medium. Any of the polyols (sugar alcohols) can be used, with the preferred one being mannitol. For the preparation of yeast extract, *Saccharomyces cerevisiae* is a preferred yeast starting material, although several other yeast strains may be useful to produce yeast ferment materials used in the compositions and methods described herein. Additional yeast strains that can be used instead of or in addition to *Saccharomyces cerevisiae* include *Kluyveromyces marxianus*, *Kluyveromyces lactis*, *Candida utilis* (Torula yeast), *Zygosaccharomyces*, *Pichia pastoris*, and *Hansanula polymorpha*, and others known to those skilled in the art.

In instances in which the substance is applied to a plant growth medium, at least one bacterial culture or at least one inoculum of the present invention can be applied to a plant or plant seed in the plant growth medium, or to the plant growth medium. Preferably, the inoculum is applied to the plant growth medium as a solid or liquid formulation. The bacterial culture or inoculum and the chemical can be applied contemporaneously or at separate times. The exact order is not of great relevance, and the optimal combination can be determined empirically by one of ordinary skill in the art without due experimentation. For example, a skilled artisan can set up experimental conditions wherein: (1) the inoculum or bacterial culture and the substance are administered concurrently, (2) the inoculum or bacterial culture is administered on a separate occasion after the substance is added to a plant growth medium, (3) the inoculum or bacterial culture is administered on a separate occasion prior to the substance being added to a plant growth medium, and the like. The results of such and similar experimental designs can easily demonstrate the most suitable methods for application of the bacterial strain or inoculum and the substance. Thus, the bacterial culture or inoculum of the present invention can be applied to a plant growth medium prior to, concurrently with, or after planting of seeds, seedlings, cuttings, bulbs, or plants in the plant growth medium.

The plant growth medium includes soil, water, an aqueous solution, sand, gravel, a polysaccharide, mulch, compost, peat moss, straw, logs, clay, or a combination thereof. Preferably, the plant growth medium is soil or compost. As is known in the art, the plant growth medium can be stored for future planting.

For purposes of the compositions and methods of the present invention, the plant can be a dicotyledon, a monocotyledon or a gymnosperm.

The stimulation of plant growth achieved by the present methods can be measured and demonstrated in a number of ways. Stimulation of plant growth can be shown in instances wherein the average height of the plant is increased by at least about 5%, by at least about 10%, by at least about 15% or by at least about 20% as compared to the average height of plants grown under the same conditions but that have not been treated with the bacterial culture or inoculant. Also, stimulation of plant growth can be shown in instances wherein the average leaf diameter of the leaves of plant is increased by at least about 5%, by at least about 10%, by at least about 15% or by at least about 20% as compared to the average leaf diameter of plants grown under the same conditions but that have not been treated with the bacterial culture or inoculant.

The present invention is also directed to plant seeds, which are coated with any of the inoculums or bacteriologically pure bacterial cultures of the present invention. The seed can be from any of the plants discussed in the foregoing sections belonging to monocotyledons, dicotyledons or gymnosperms. The bacterial inoculant or culture can be applied to the seeds through the use of a suitable coating mechanism prior to the seeds being sold into commerce for planting. The process of coating seeds with such an inoculum is generally well known to those skilled in the art. For example, the bacteria can be mixed with a porous, chemically inert granular carrier as described by U.S. Pat. No. 4,875,921, which is incorporated herein by reference with respect to such carriers. Alternatively, the bacterial inoculant can be prepared with or without a carrier and sold as a separate inoculant to be inserted directly into the furrows into which the seed is planted. The process for inserting such inoculants directly into the furrows during seed planting is also generally well known in the art. The density of inoculation of these bacterial cultures onto seeds or into the furrows should be sufficient to populate the sub-soil region adjacent to the roots of the plant with viable bacterial growth.

The present invention also relates to kits for stimulating plant growth, which include an inoculum as described herein, and instructions for applying the inoculum to plants, plant seeds, or a plant growth medium. Kits containing inoculants of the invention will typically include one or more containers of the inoculant, and printed instructions for using the inoculant for promoting plant growth. The kit can also include tools or instruments for reconstituting, measuring, mixing, or applying the inoculant, and will vary in accordance with the particular formulation and intended use of the inoculant.

Bacteria provide a good system in which to select mutations for desired characteristics. It is possible to force such mutations through proper selection of desirable traits, while retaining the desired plant growth-promoting capabilities in bacteria. Accordingly, traits that may be desirable to induce in bacterial strains disclosed herein by forcing mutations without affecting plant growth promotion include, but are not limited to, antibiotic resistance, heavy metal resistance, tolerance to heat and cold, high and low salt tolerance, metabolic deficiencies (such as requirements for certain amino acids), metabolic gain-of-function (such as the ability to metabolize polysaccharides or plastic compounds), ability to withstand desiccation, resistance to UV radiation, tolerance of man-made chemicals, ability to bind more tightly to plant roots, higher affinity for plants, increased ability to colonize plants, motility, ability to accept recombinant DNA, and ability to express exogenous proteins. These attributes can be garnered by use of selective pressure or through man-made manipulation of plant growth promoting bacteria's genetics.

Further details concerning the preparation of bacterial inoculants and methods for inoculating plants with bacterial inoculants are found in e.g. U.S. Pat. Nos. 5,586,411; 5,697,186; 5,484,464; 5,906,929; 5,288,296; 4,875,921; 4,828,600; 5,951,978; 5,183,759; 5,041,383; 6,077,505; 5,916,029; 5,360,606; 5,292,507; 5,229,114; 4,421,544; and 4,367,609, each of which is incorporated herein by reference with respect to such methods.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1: Enhancing Sustainable Agriculture by Unraveling Plant-Microbiome Interactions Dependent on Rare Earth Element Plant-associated microbes play essential roles in plant growth and health and possess numerous plant-growth promoting traits (PGPT). Some reported bacterial PGPT include: production of metabolites/enzymes that increase phosphate solubilization; production of protein/metabolites that mobilize metals (particularly iron); production of compounds modulating plant growth hormones: cytokines, gibberellins, auxins; and the enzyme 1-aminocyclopropane-1-carboxylate deaminase. Additionally, in the rhizosphere some bacteria can mediate nitrogen fixation. A greater understanding of the mechanisms leading to the bacterial stimulation of plant growth will improve selection and utilization of strains with efficient PGPT.

*Methylobacterium* are dominant members of the phyllosphere microbiota, and one species in particular—*M. extorquens*—has served as a model system for both understanding phyllosphere-plant interactions. Strains of this species have been reported to moderately increase plant growth. *M. extorquens* is a facultative methylotroph that has been studied extensively—both genetically and biochemically—for nearly 60 years to uncover the biochemical pathways required for growth on single-carbon compounds. A sequenced genome and a wide variety of genetic tools are available for its study. Proteomics, transcriptomics (RNA-seq), and metabolomics extractions and pipelines for analysis have also been optimized, as well as enzymatic assays.

In *M. extorquens*, methanol utilization begins by oxidation of methanol to formaldehyde in the periplasmic space. Until recently, it was believed that this reaction was catalyzed solely by the extensively-studied Ca-dependent MeDH encoded by the mxaFI genes (MxaFI). However, the genome sequence of *M. extorquens* revealed two xoxF genes, xoxF1 and xoxF2, which are 90% identical to each other and encode proteins that share 50% amino acid identity with the MxaF subunit of the Ca-dependent MeDH. In 2012, Nakagawa et al. demonstrated that when MeDH was purified from *M. extorquens* cells grown in medium containing La, the pure XoxF enzyme contained 1.2 atoms of La and lacked Ca. Ecosystems where methylotrophs are abundant contain nanomolar or greater concentrations of REE.

REE-*M. extorquens* Interaction Enhances Plant Growth.

Applicants hypothesized that REE do not increase plant growth directly, but rather, increase plant growth indirectly via stimulation of the *Methylobacterium* community, and that it is these members of the plant microbiome that exert the stimulatory effect upon the plants. Applicants tested this hypothesis with both soybean and the common bean, and demonstrated for the first time that methylotrophs and REE act synergistically to enhance plant growth.

Figure 2:
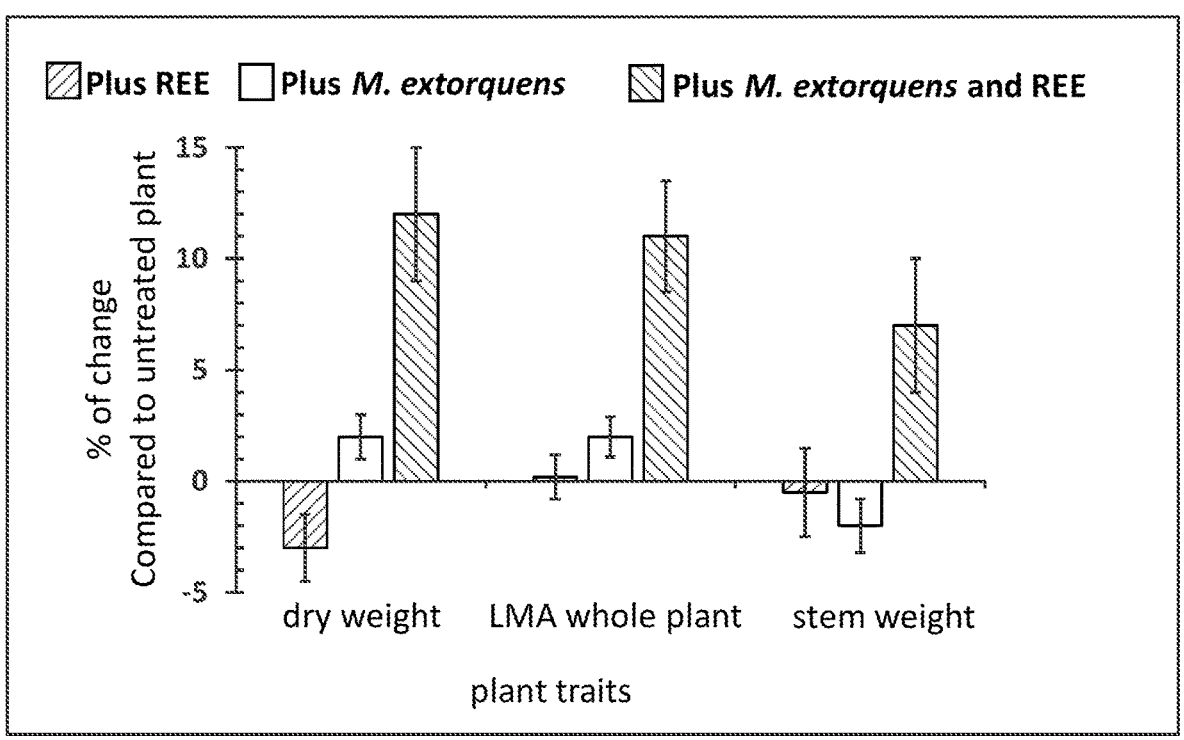
FIG. 2 shows REE-dependent methylotrophy enhancing plant growth. When both REE and *M. extorquens* are present, an enhancement of growth is observed when compared to La only or methylotroph only condition.

To identify if *M. extorquens* mediates the REE effect on plant growth, growth yields comparing presence and absence of *M. extorquens* plus REE were determined (FIG. 1). A comparison of cell dry weight, and leaf mass per area (LMA) between plants after inoculation of either La (0.5 μM), *M. extorquens*, and La plus *M. extorquens* showed differences in yield with respect to the no-inoculation control (FIG. 2) corroborating REE-*M. extorquens* mediated enhancement of plant growth. This is the first evidence of a synergistic effect on plant growth when both methylotroph and REE are inoculated.

Changes in Methylotrophy in the Presence of REE Produce Potential PGPT.

PGPTs that have been described include: 1-aminocyclopropane-1-carboxylic acid (ACC) deaminase activity, indole acetic acid (IAA) production, $N_2$ fixation, phosphate solubilization, pyrroloquinoline quinone (PQQ) synthesis, siderophore production, plant disease suppression as well as methanol, sucrose, and betaine utilization.

To identify mechanisms by which *M. extorquens* can sense and acquire REE, as well as to support REE-dependent methanol growth, Illumina-based transcriptome analyses (RNA-seq) was performed. Comparison of cells grown in liquid culture with and without REE addition allowed us to identify changes that may be relevant in planta.

Figure 3:
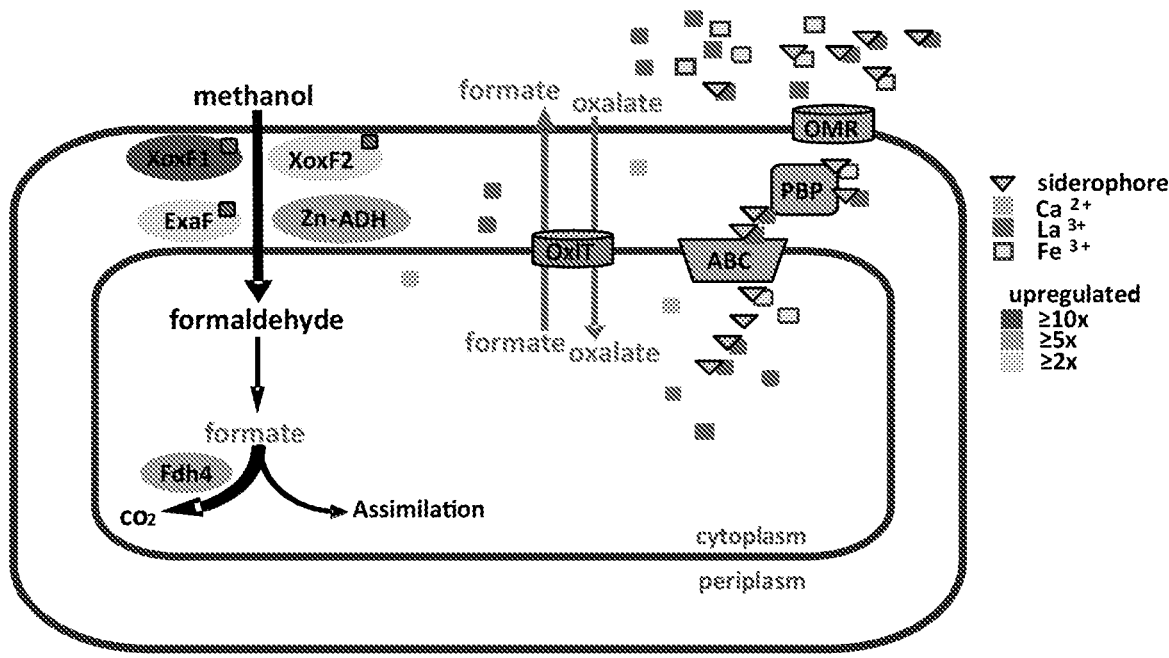
FIG. 3 shows a model summarizing putative REE-sensing, oxidation and assimilation bacterial systems. Scheme of methanol utilization with La in the medium. ABC, ABC transporter; PBP, periplasmic binding protein; OMR, outer membrane receptor. Fold differences are compared to Ca growth.

Of special interest among the REE-upregulated genes were upregulation of four alcohol dehydrogenases (XoxF1 and XoxF2; ExaF; and a Zn-containing alcohol dehydrogenase Zn-ADH), an ABC transporter potentially involved with metal transport, and enzymes involved in formate metabolism. The $La^{3+}$-upregulated genes were those encoding the methanol dehydrogenase, XoxF1 and XoxF2 (10-fold); a putative alcohol dehydrogenase quinoprotein (ExaF; 3.4-fold), a Zn-containing alcohol dehydrogenase (Zn-ADH; 4.8-fold): changes in these enzyme activities would affect methanol utilization; upregulation of the PQQ synthesis pathway (10-fold); an ABC transporter (6.3-fold): potentially involved with siderophore transport; and enzymes involved in oxalate and formate metabolism: formate dehydrogenase (Fdh4; 4-fold), formyl-CoA transferase (Frc12; 3-fold), and oxalyl-CoA (Oxr; 2.5-fold) (FIG. 3). It has been suggested that Fdh4 is the most crucial Fdh in methanol metabolism though it is the one we know the least about. It is intriguing to speculate that the reason why Fdh4 activity has never been detected is because it may require REEs. Frc12 and Oxr are enzymes of the oxalyl-CoA pathway (OXC). This pathway is known to produce glyoxylate when *M. extorquens* is grown with oxalate as a carbon source. Upregulation of this metabolic pathway suggests excretion of organic acids is increased in the presence of $La^{3+}$.

Figure 4:
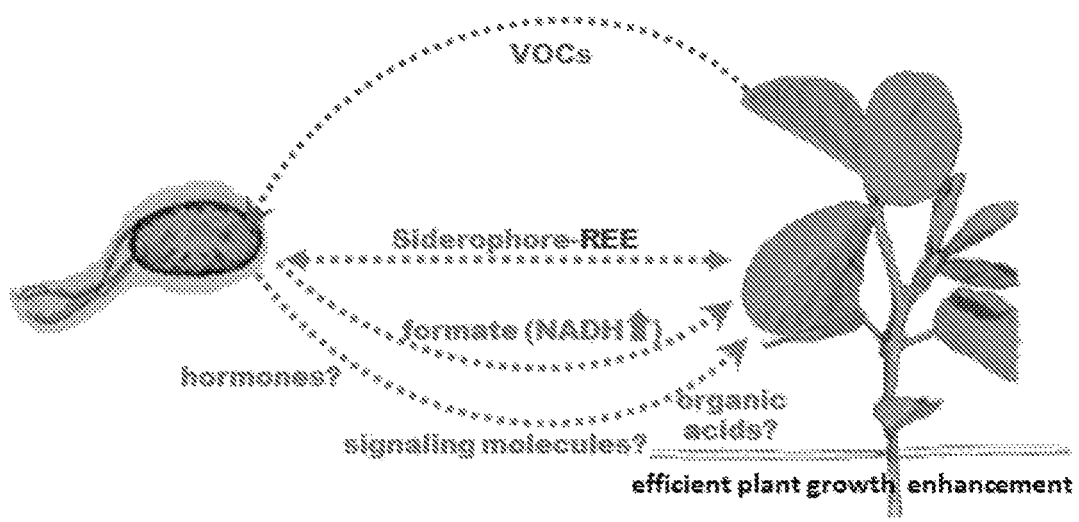
FIG. 4 shows molecular mechanisms suggested to enhance plant growth by REE and *Methylobacterium* in the phyllosphere.

Liquid chromatography analysis corroborated higher accumulation of formate (5-fold) in extracts from cells grown on methanol plus REE. Accumulation of formate will result in excretion, which can then facilitate mobilization of insoluble metals in the phyllosphere so that they may become available to the plant cells. Additionally, excretion of a molecule that can bind La was observed through UV-Visible and fluorescence analysis (peak at 360 nm; excitation 350). This suggests a "siderophore-like" mechanism for acquisition of REE and potential mobilization of numerous metals including iron. Thus, based on transcript levels and initial metabolite and biochemical analysis, potential pathways supporting $La^{3+}$-dependent growth affecting PGPTs were identified (FIG. 4).

Diverse REE are Involved in Methanol Metabolism.

Figure 5A:
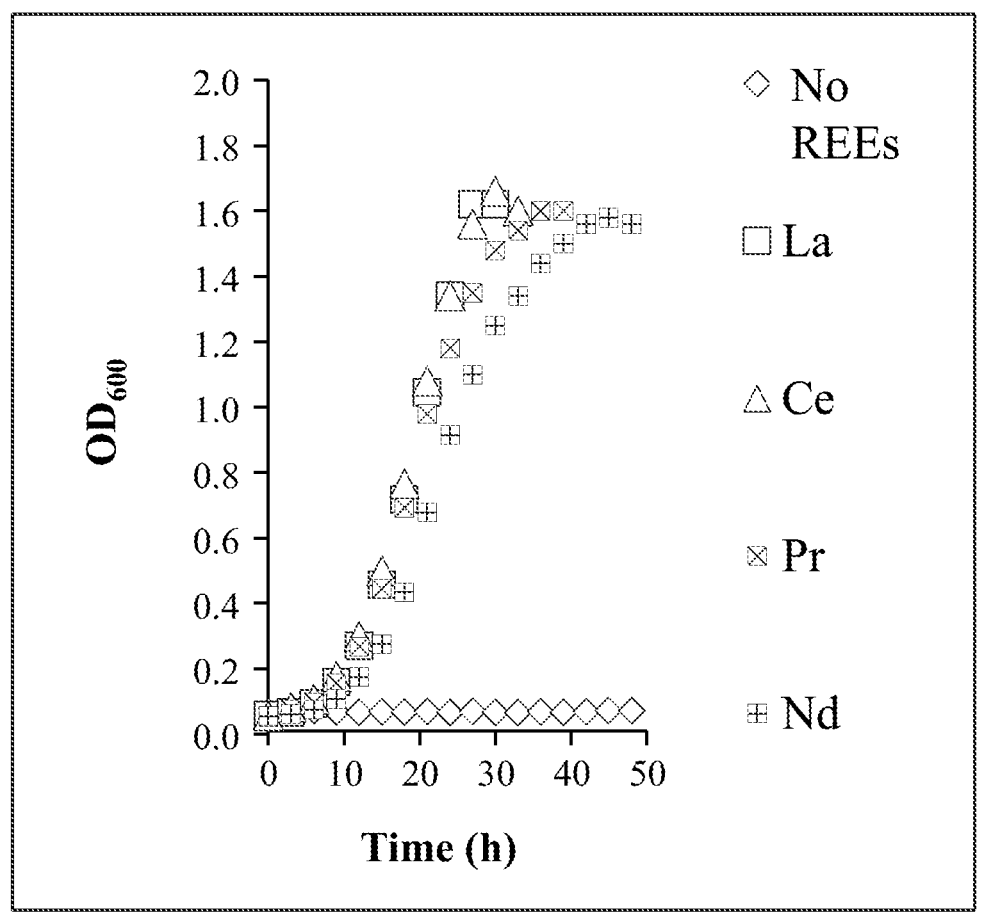
FIGS. 5A-5B show REE-dependent methylotrophy.

Phenotypic studies were developed to determine if all REE used in fertilizers had an effect on methylotrophy. All lanthanides are considered strong Lewis acids, and similarities in their atomic radii due to lanthanide contraction suggest that transport and catalytic properties may be shared among all elements in the series. There is a direct link between REEs commonly used in fertilizers, such as La, $Ce^{3+}$, $Pr^{3+}$, and $Nd^{3+}$, and growth of *M. extorquens* using methanol as carbon source (FIG. 5A). $La^{3+}$ or $Ce^{3+}$ have been found to bind to the active site of the methanol dehydrogenase XoxF. Elements larger than samarium ($Sm^{3+}$) are unable to support bacterial growth on methanol above background (no REE addition) suggesting that as the ionic radii decreases, the less these elements are able to function as cofactors for alcohol dehydrogenases. Alternatively, it is possible that the remaining lanthanides are not transported into the cell. Detailed biochemical analyses are required to distinguish between these two possibilities.

Figure 5B:
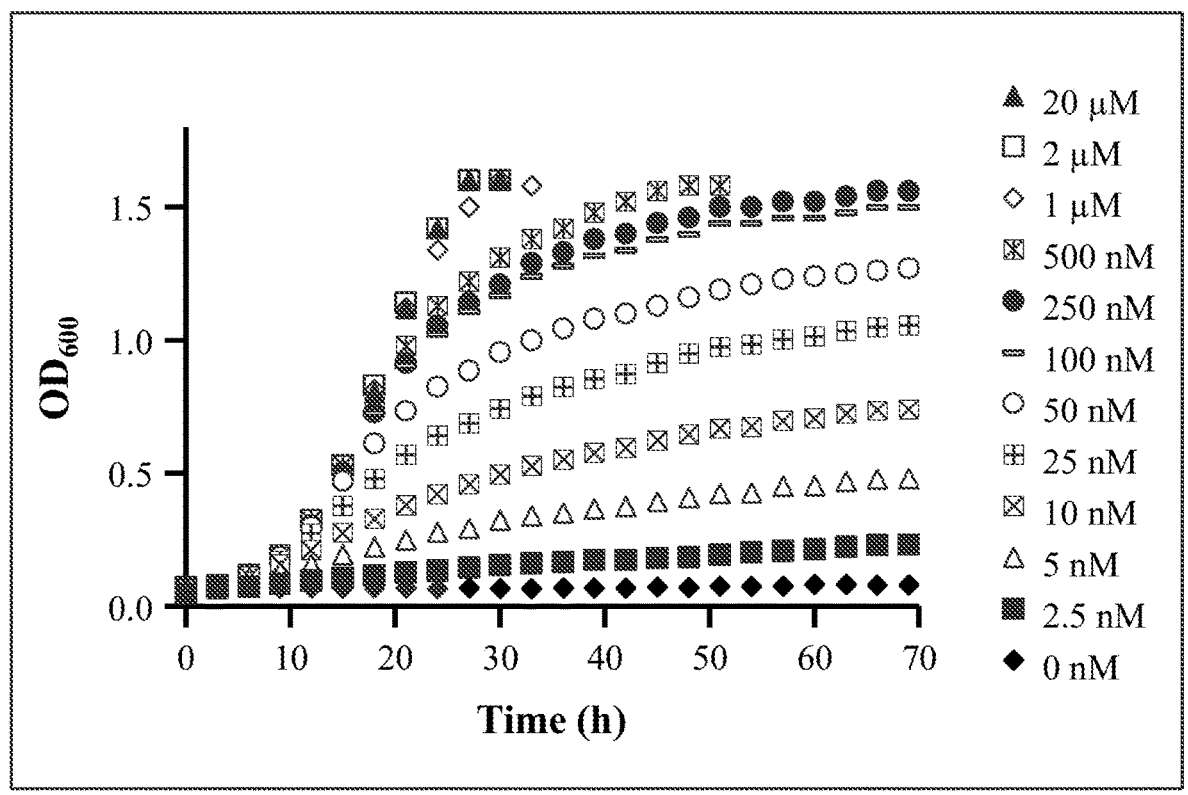

The concentrations of exogenous $La^{3+}$ that would support $La^{3+}$-dependent methanol growth were assessed using methanol medium supplemented with $La^{3+}$ concentrations ranging from 0-20 µM (FIG. 5B). The mxaF mutant strain was used to eliminate any contribution by the $Ca^{2+}$-dependent methanol dehydrogenase MxaFI. $La^{3+}$-dependent methanol growth, albeit poor growth, was observed using $La^{3+}$ concentrations as low as 2.5 nM while 1 µM $La^{3+}$ resulted in maximal growth rate and a final $OD_{600}$ of 1.6.

Example 2: REE-Metabolic Network Enhancing Plant Growth Via Rhizobacteria

Bacteria rely primarily on carbohydrate or alcohol metabolism to access scarce nutrients in the phyllosphere. PGPTs include high expression of outer membrane proteins (porins, TonB receptors), higher methylotrophic activity mainly by methanol dehydrogenases, and upregulation of ABC-transport systems for carbohydrates and amino acids. Another trait is high abundance of carbon storage (phasin) and stress-related proteins (chaperons GroEL). Methanogenesis and methane oxidation, dinitrogen fixation, chemotaxis and motility are also activities contributing to plant growth that occurs in the phyllosphere. *Methylobacterium extorquens* is a predominant member of the phyllosphere microbiota due to the ample availability of methanol, a byproduct of pectin esterases during the demethoxylation of pectin of growing leaves and stomatal opening.

In contrast, in the rhizosphere simple carbon sources in roots are available through the process of root exudation (sugars, amino acids, aliphatic acids). Roots and rhizosphere PGTPs include adhesion, stress responses, secretion (type IV), host-pathogen, microbe-microbe and phage-microbe interactions, as well as iron mobilization (in soybean this mobilization occurs using heme and hemin uptake), and sugar transport. Some mechanisms are known, for example: phosphorus-utilization occurs via increased activity of alkaline phosphatase; metabolic pathways upregulated include: myo-inositol 1-monophosphatase, epi-inositol hydrolase; glutamine-, glutamate-, aspartate- and asparagine-biosynthesis; glyoxylate synthesis, and production of secondary metabolites.

Shared PGPTs between rhizosphere and phyllosphere include higher activity of citrate synthase, and glycosyltransferase, acquisition of nitrogen, phosphorus uptake via alkylphosphonate utilization, and potassium and iron (heme, hemin) uptake.

Biogenic volatile organic carbon molecules (BVOCs) are a complex mixture of relatively small (molecular masses less than 300 Da) lipophilic compounds that play many roles in the biosphere. The most abundantly produced BVOC is isoprene, which is known to affect plant gene expression but whose physiological function remains obscure. Two BVOCs have been proposed as methods by which plants "talk" to one another. These are the methyl esters of two critical signaling molecules, jasmonic acid (JA) and salicylic acid (SA). There are clear atmospheric volatile signals that are ecologically important. Some of these result in the fascinating tritrophic response in which plant volatiles attract parasites of herbivores (the enemy of my enemy is my friend). Less well known are substantial findings of volatile signals exchanged between bacteria and fungi and plants. Some of the compounds involved are known; 2,3-butanediol and acetoin are two volatiles important in affecting growth and immunity of plants. But it is likely there are many other volatiles that affect plant growth and defense. Bacterial volatiles are known to affect carbon metabolism of plants and are known to affect SA and JA signaling.

The role of volatile signals in the rhizosphere is attracting significant attention. Unlike in the atmosphere, signal dilution of a volatile compound would not be as problematic in the soil. It may be that volatile signals in the soil are very common. Given some of the stimulatory effects of microbial volatiles on plant growth, the volatile interactions in the soil may be a very fertile area of research to help discover how plant resilience can be enhanced. Signaling in the rhizosphere can be from microbe to microbe, microbe to plant, plant to microbe, or plant to plant. It is even possible that the controversial findings of methanol stimulation of plant growth and yield published in the 1990s but which were sometimes not replicated, might be understood by a more comprehensive look at the role of volatiles and plant microbe interactions given the role of REEs on methylotrophs. Soybean growth in particular was found to be stimulated by methanol treatment. Root BVOCs include alcohols, aldehydes and ketones, sulfur compounds, terpenoids, aromatic compounds, furans, esters, and organic acids. Of special interest are 2-pentyl-furan, dimethyl sulfide, ethyl acetate, acetic acid, acetone, ethanol, and hexan-1-ol, 3-octen-3-ol, as these BVOCs are produced by both plants and bacteria. Because rhizobacteria have been shown to both promote plant growth and modulate root-system architecture via BVOC emission, it is pivotal to study if REE-bacterial metabolism affects the volatilome, and if so to define the BVOCs involved as a first step toward finding molecular mechanisms and exploiting these interactions for improved crop resilience.

Figure 6:
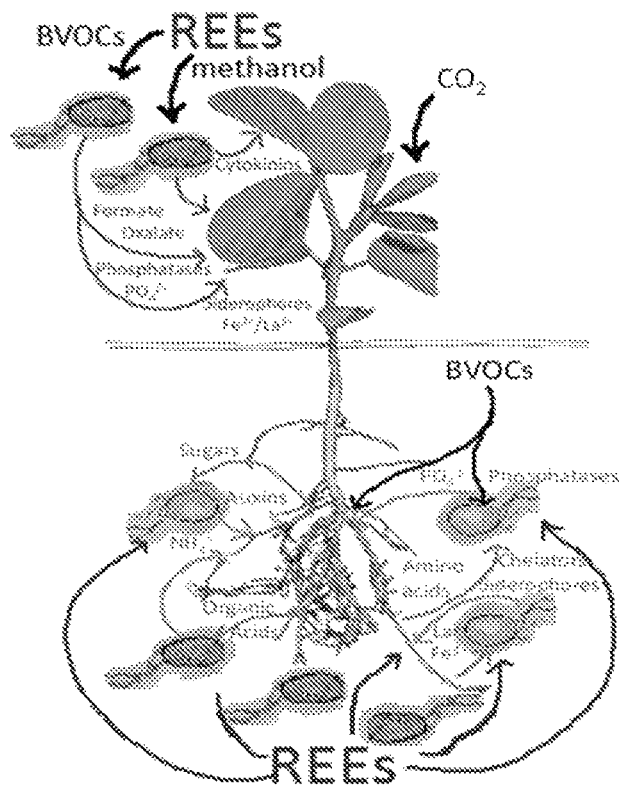
FIG. 6 shows molecular mechanisms suggested to enhance plant growth by REE and *M. extorquens* or *B. diazoefficiens*.

By studying two plant environments (phyllosphere and rhizosphere) complementary mechanisms are identified as microbes of each environment are known to have different roles in the plant (FIG. 6). Studying the volatilome profile above and below ground provides insights into the molecular basis associated with plant growth and BVOCs. Together, these studies allow us to better engineer microorganisms to further sustainable agriculture. With the identification of the plant growth-promotion traits, the microbes can be engineered to constitutively produce the compounds, and reduce or eliminate the use of fertilizers.

Initial biochemical studies identified REE-containing quinoproteins that are not unique to one-carbon metabolism or methylotrophy. An ethanol dehydrogenase (homolog of ExaA, $C_2$ metabolism) and glucose dehydrogenase (Gcd, $C_6$ metabolism) use $La^{3+}$ for catalysis, suggesting that microbes other than methylotrophs can use REEs for metabolic function. These metabolic changes can be further studied using a member of the rhizobiome, *Bradyrhizobium diazoefficiens* (formerly *Bradyrhizobium japonicum*), a rhizobacteria that contains homologs of the REE-containing quinoproteins that we have identified.

Example 3: Community Identification of the Rare Earth Dependent Plant Probiotic

Figure 7:
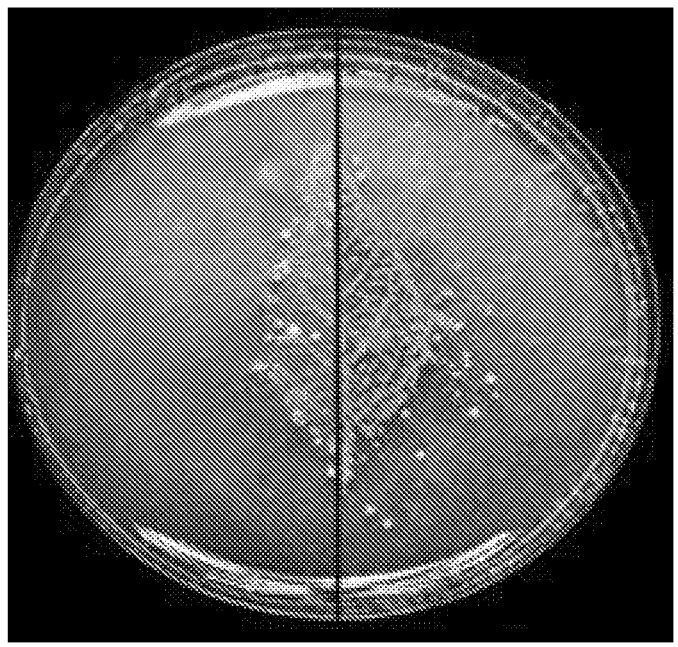
FIG. 7 shows a leaf print on a plate with minimal media and methanol without (left) and with (right) REE. Abundant isolation of methylotrophs is observed when REE are present as a result of differences in methylotrophic metabolism.

Most of the current isolated methylotrophs are strains that contain a methanol dehydrogenase system dependent on calcium (MxaFI) that can substitute the function of XoxF or ExaF. However, genomic analysis of environmental samples has demonstrated that the majority of methylotrophs contain XoxF and/or ExaF instead of MxaFI. Consistent with this analysis, the addition of REE to the working media allows isolation of methylotrophs that were previously unculturable (FIG. 7).

Although the vast majority of physiological analyses have occurred with just a few strains of *M. extorquens*, members throughout the genus are recovered as isolates from both the phyllosphere and rhizosphere. Initial data was generated using the well-characterized plant isolate *M. extorquens* PA1, but there remains a huge untapped potential for increased efficacy of plant growth stimulation using novel environmental strains.

Although methanol and formate use appears to be essentially ubiquitous, there is a great diversity in the use of other single-carbon compounds, such as methylamine, as well as in the ability to grow with multi-carbon compounds such as ethanol, oxalate, propanol, valeric acid, betaine, sugars, etc. Some strains can even fix atmospheric nitrogen in nodules or grow phototrophically. However, the impact of environmental changes upon the *Methylobacterium* community is unknown, not to mention how this may enhance or diminish plant growth promoting traits.

Isolation of Novel REE-Dependent Methylotrophic Strains.

Applicants have isolated methylotrophic strains both in the presence and absence of REE from the phyllosphere from soybean plants grown in agricultural fields in Michigan. 100 colonies were obtained while adding REE and methanol, and 80 colonies were isolated on methanol media without REE. Phenotypic studies confirm these pink methylotrophs exhibit clear differences in growth rates, morphology, biofilm formation, etc. 16S rRNA amplicon analysis is used to identify each strain and compare the differences among the +REE community and the −REE community.

Identification of Isolates Via 16s RNA Amplicon Analysis

Figure 8:
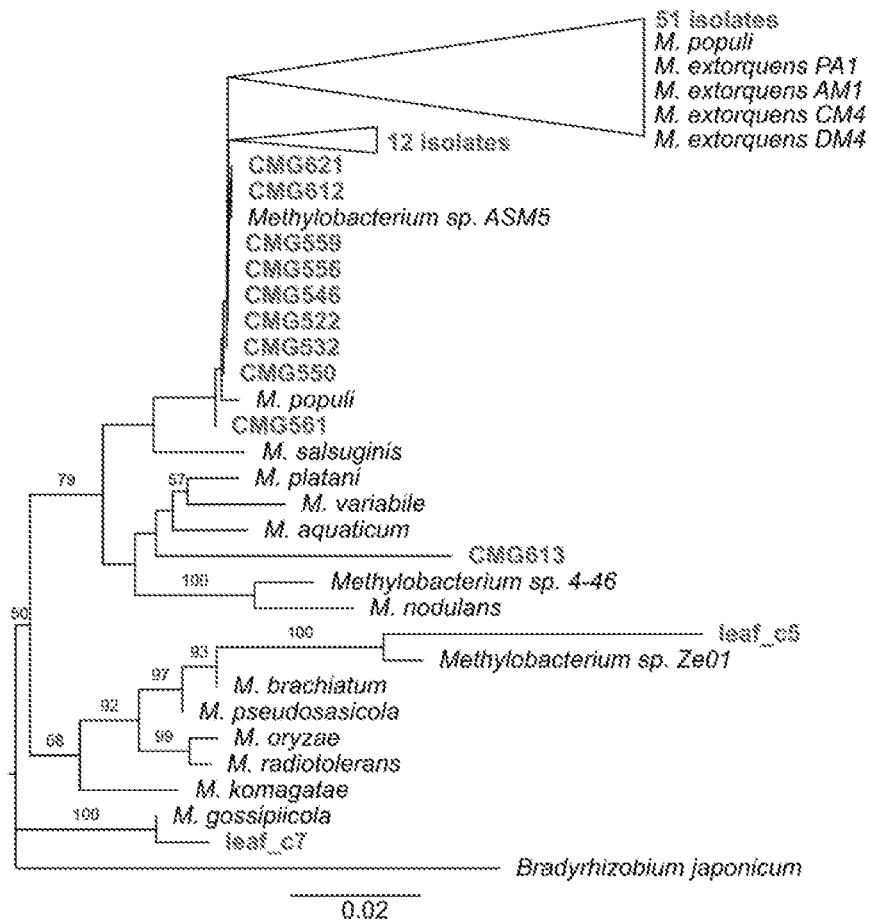
FIG. 8 shows phylogenetic and genomic diversity of *Methylobacterium*. The strains isolated from soybean plants are closely related. Isolates from phyllosphere of soybean and reference species. ML tree of 16S rRNA.
Figure 9:
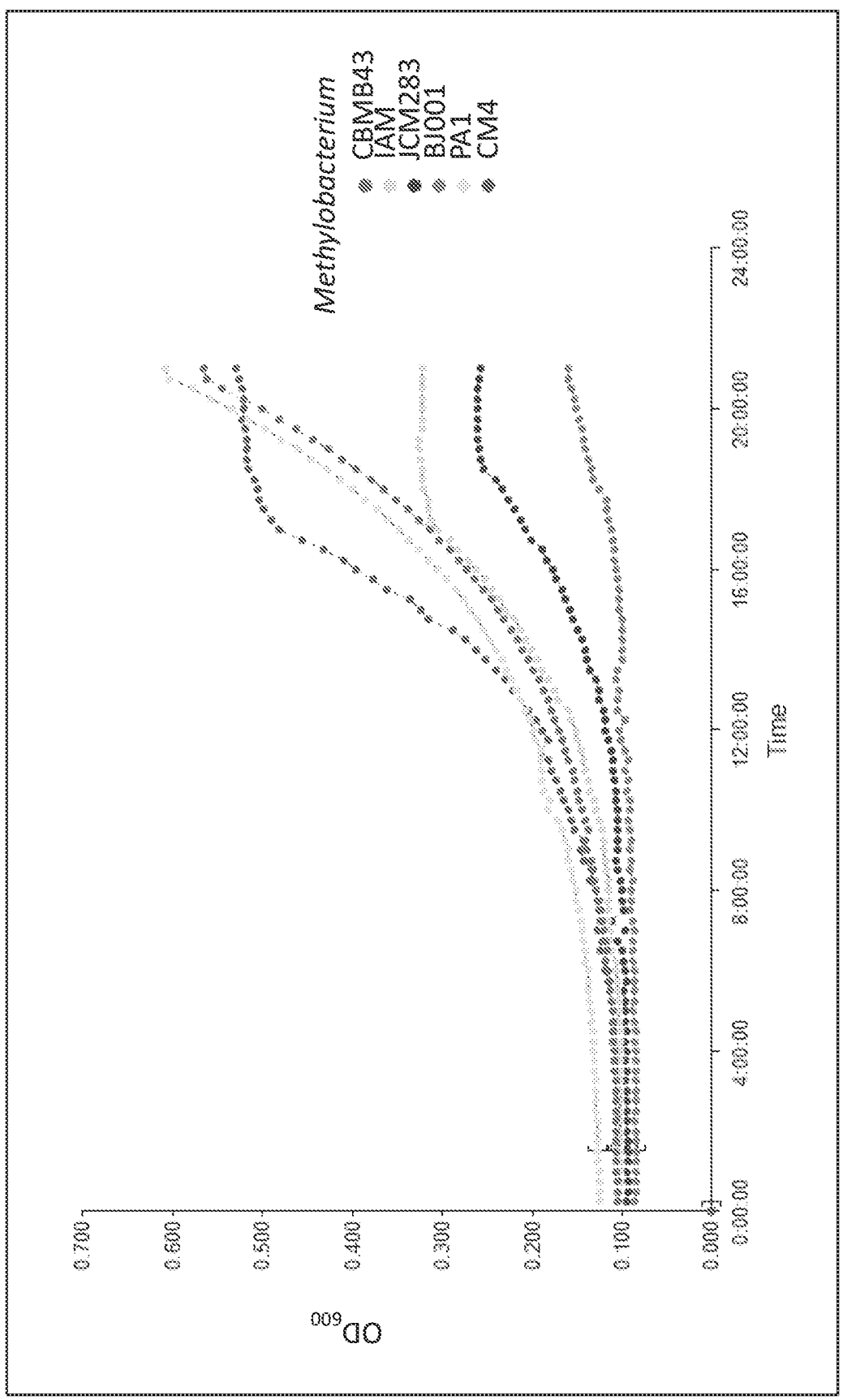
FIG. 9 shows representative growth of diverse isolates. *M. extorquens* PA1 is the reference strain with a doubling time of 3.7 hours when grown on methanol. Numerous isolates have differences in growth rate. Strain CBMB43 has a 33% increased growth rate when compared to PA1 for a doubling time of 2.4 hours.

When comparing strains isolated in the presence (50) and absence (50) of REE, both unique and common strains were obtained (FIG. 8). All isolates are pink methylotrophs and belong to the genera *Methylobacterium*. Although diversity of the isolated strains from soybean is limited, numerous differences among isolates were found: e. g. different growth rates, and different final yields (OD) when grown on methanol (FIG. 9). This result suggests that although at the level of 16S rRNA the isolates are similar, they can have diverse effects on excreted metabolites and therefore different effects on plant growth.

Figure 10:
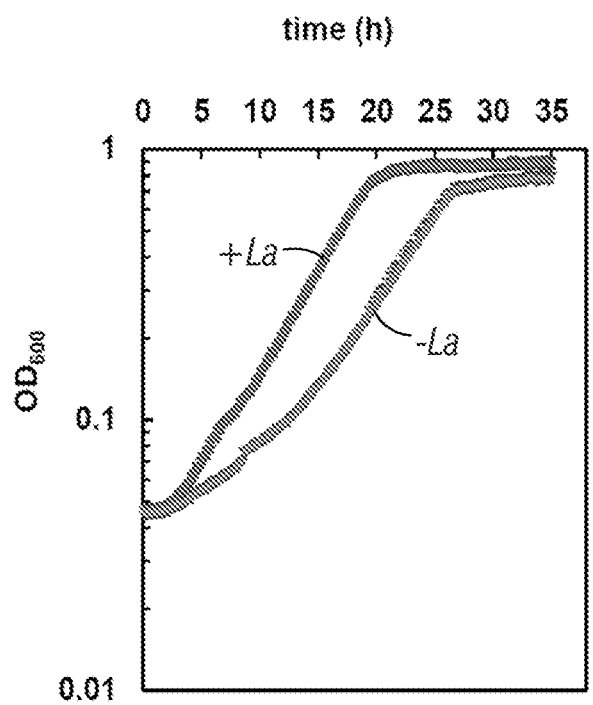
FIG. 10 shows representative growth of *M. extorquens* PA1. Addition of La increases growth rate when grown on methanol media.

Applicants predicted that addition of REE such as lanthanum (La) affects growth rate of strains, and this effect is indicative of changes in the bacterial central metabolism that lead to changes in plant-microbe interactions and effect on plant growth. Strains were identified that had increased growth, strains that had decreased growth, and strains which had no growth differences on methanol when compared to the laboratory strain, PA1 (FIG. 10).

Figure 11:
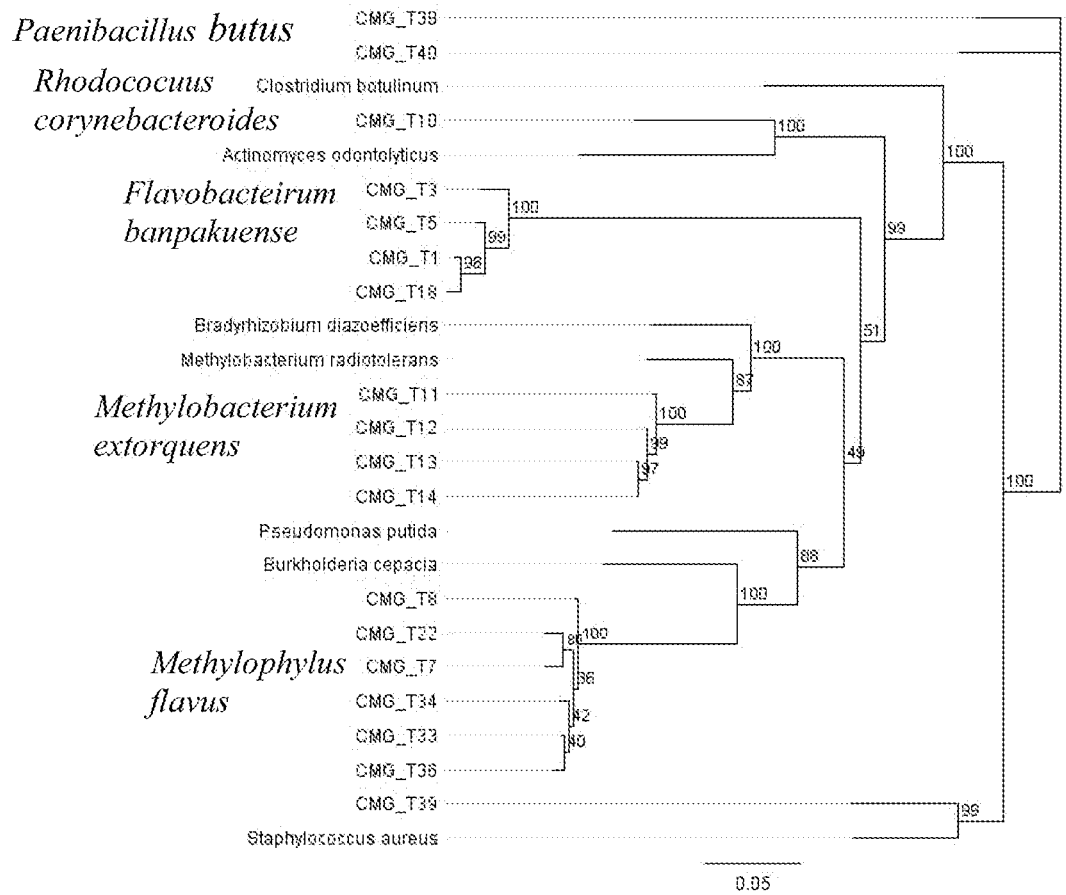
FIG. 11 shows a phylogenetic tree of isolated methylotrophic strains from tomato.

Methylotrophic strains were also isolated from tomato. When comparing the strains isolated in the presence (54) and absence (67) of REE, both unique and common strains were obtained. A broader variety and diversity of strains have been isolated as shown in the phylogenetic tree (FIG. 11).

TABLE 1

Addition of La affects growth rate of different isolates when grown on methanol media.

| | Doubling time (hours) | |
| --- | --- | --- |
| Strain | No La | Plus LA |
| PA1 | 3.7 | 3.2 |
| CMG514 | 2.9 | 2.3 |
| CMG522 | 2.6 | 6.1 |
| CMG600 | 2.5 | 2.8 |
| CMG677 | 2.6 | 2.9 |
| CMG715 | 2.5 | 2.5 |

Each type of strain was combined to formulate different probiotic mixes (Table 2): mixes of 2 strains classified as slow growers, mixes of 2 strains classified as fast growers, and mixes of 2 strains that grew as our lab strain (PA1) were further tested on soybean plants.

TABLE 2

Example of strains used for probiotic composition. Mix of 2 slow growers, mix of 2 fast growers, and 2 with same growth as lab strain (PA1).

| Strain | Doubling time (hours) | | |
|---|---|---|---|
| | No La | Plus LA | |
| PA1 | 3.7 ± 0.3 | 3.2 ± 0.1 | Lab strain |
| CMG514 | 2.9 ± 0.2 | 2.3 ± 0.2 | Fast growers |
| CMG517 | 3.1 ± 0.3 | 2.2 ± 0.3 | |
| CMG602 | 2.9 ± 0.3 | 2.9 ± 0.2 | Same growth as lab strain |
| CMG715 | 2.5 ± 0.2 | 2.5 ± 0.1 | |
| CMG802 | 3.1 ± 0.2 | 2.5 ± 0.3 | Fast growers |
| CMG803 | 3.0 ± 0.1 | 2.6 ± 0.1 | |
| CMG656 | 2.9 ± 0.2 | 3.9 ± 0.2 | Slow growers |
| CMG828 | 3.2 ± 0.1 | 4.2 ± 0.1 | |

The novel isolated strains are able to grow on sources that are not previously reported in the literature. Their metabolic changes are beyond one-carbon metabolism, including sugars and aromatic amino acid metabolism (Table 3).

TABLE 3

Growth comparison of diverse strains in different substrates with respect to general methylotroph, strain PA1.

| Strain | Methanol | Formate | Acetate | Butanol | Fructose | Glucose | Tyrosine |
|---|---|---|---|---|---|---|---|
| PA1 | ++ | ++ | ++ | − | − | − | − |
| CMG516 | ++ | ++ | − | − | ++ | − | − |
| CMG518 | ++ | ++ | + | ++ | + | − | − |
| CMG521 | ++ | ++ | + | + | ++ | − | − |
| CMG575 | ++ | ++ | + | − | + | ++ | ++ |
| CMG576 | ++ | ++ | + | − | ++ | − | + |
| CMG800 | ++ | ++ | + | ++ | − | − | + |
| CMG801 | ++ | ++ | ++ | + | − | − | + |
| CMG802 | ++ | ++ | + | + | − | − | ++ |

++, Fast and efficient growth;
+ Growth but low yields;
−, No growth

Determination of the Effect on Plant Growth by REE-Dependent Strains

Figure 12:
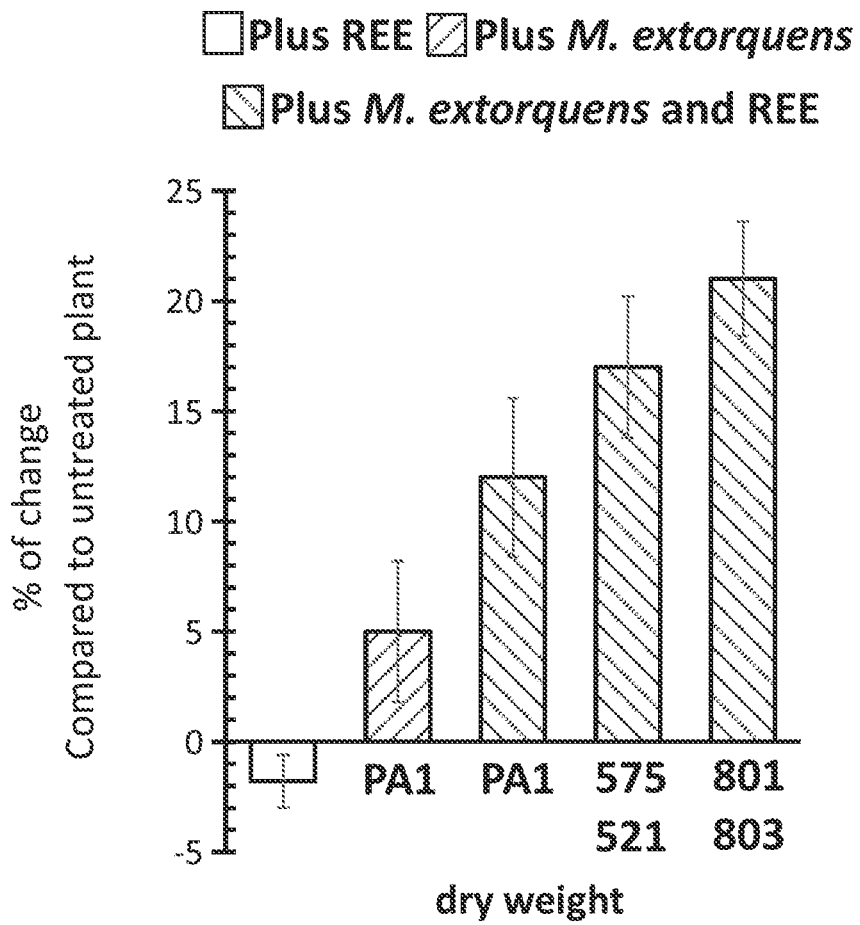
FIG. 12 shows the effect of probiotics on plant growth, parameter measured dry weight.

Sixteen isolated strains were tested including 8 from soybean, and 8 from tomato in mixes of two. Pairs of fast growers, slow growers, and strains that grew as PA1 were used. A mix of two strains (Fast growers) isolated from soybean incremented soybean growth by 17% when compared to soybean grown without probiotic inoculation, and by 6% when compared to soybean inoculated with *M. extorquens* PA1 (FIG. 12). Two strains isolated from tomato incremented soybean growth by 21% when compared to soybean grown without probiotic inoculation, and by 9% when compared to soybean inoculated with *M. extorquens* PA1.

Example 4: Methylotroph Isolation

Materials
Sterile 50 mL Falcon tubes
50 mM phosphate buffer pH 7.3
Prepare plates by using Minimal medium (PIPES based)[1]+adding RPMI 1640 Vitamins Solution*+50 μg/mL cycloheximide, with and without 2 M lanthanum chloride+50 mM Methanol.

[1]Delaney, N. F., Kaczmarek, M. E., Ward, L. M., Swanson, P. K., Lee, M. C., and Marx, C. J. (2013). Development of an optimized medium, strain and high-throughput culturing methods for *Methylobacterium extorquens*. PLoS ONE 8:e62957.

Procedure
1. Collect leaf in sterile tubes 50 mL Falcon tubes
2. Add 50 mL of phosphate buffer and vortex at maximum speed at room temperature for 5-10 minutes.
2a. Modification: Add 10 mL per leaf, and break cells using a mortar and pestle. Transfer the suspension to a falcon tube and incubate on ice for 20 min. keeping on ice, sonicate the suspension using six cycles of 30 seconds.
3. Transfer 100 μL of the suspension to a plate of minimal medium with lanthanum chloride and plates without lanthanum chloride (suspension as is and serial dilutions to 1/1000) and incubate at 30° C. in the dark to protect the cycloheximide.
4. Centrifuge remaining liquid at 3900 RPM at 4° C.
5. Remove the supernatant in order to concentrate in about 500-1000 μL for glycerol stock and/or DNA extraction.
6. After 4 days of incubation, pick isolated, pink colonies from the spread plates and streak for isolation onto Plates of minimal medium with methanol+vitamins and cycloheximide. Streak colonies from the +La plates onto +La media and the colonies from the −La plates onto −La media. Incubate at 30° C. in the dark.
7. After 4 days of incubation, pick isolated, pink colonies from the streak plates and inoculate into liquid minimal medium with vitamins, +/−La as appropriate. Grow overnight at 30° C. shaking at 200 RPM.
8. For isolates that grew in liquid media (confirming their ability to grow on methanol), prepare a freezer stock with 500 μL of culture and 25 μL filter-sterilized DMSO. Freezer at −80° C. for future use.

What is claimed is:
1. A method for stimulating plant growth comprising: applying an inoculum comprising methylotrophic bacteria and one or more rare earth elements to a plant, plant seed, or plant growth medium, wherein the methylotrophic bacteria and the one or more rare earth elements act synergistically to stimulate plant growth.
2. The method of claim 1, wherein the inoculum causes upregulation of one or more alcohol dehydrogenases in the methylotrophic bacteria.

3. The method of claim 2, wherein said alcohol dehydrogenases include one or more of XoxF1, XoxF2, ExaF, or Zn-ADH.

4. The method of claim 1, wherein the inoculum causes upregulation of one or more enzymes in alcohol metabolism.

5. The method of claim 1, comprising applying the inoculum to the plant growth medium.

6. The method of claim 5, comprising applying a liquid or solid formulation of the inoculum to the plant growth medium.

7. The method of claim 5, comprising applying the inoculum to the plant growth medium prior to, concurrently with, or after planting of seeds, seedlings, cuttings, bulbs, or plants in the plant growth medium.

8. The method of claim 1, comprising applying the inoculum to plant leaves, roots, or stems.

9. The method of claim 1, comprising applying the inoculum to plant seeds.

10. The method of claim 9, comprising coating plant seeds with the inoculum prior to planting.

11. The method of claim 1, further comprising storing the plant growth medium for future planting.

12. The method of claim 1, wherein the plant growth medium comprises soil, water, an aqueous solution, sand, gravel, a polysaccharide, mulch, compost, peat moss, straw, logs, clay, or a combination thereof.

13. The method of claim 12, wherein the plant growth medium comprises soil or compost.

14. The method of claim 1, wherein the plant is a monocot, dicotyledon or gymnosperm.

15. The method of claim 1, wherein the dry weight of said plant is increased by 12-15%.

16. The method of claim 1, wherein the methylotrophic bacteria comprise *Methylobacterium extorquens*.

17. The method of claim 1, wherein the rare earth element is lanthanum, cerium, praseodymium, and/or neodymium.

18. The method of claim 17, wherein the lanthanum, cerium, praseodymium, and/or neodymium are in the form of a nitrate, oxide, or chloride.

19. The method of claim 1, wherein the rare earth element is lanthanum.

20. The method of claim 19, wherein the lanthanum is in the form of a nitrate, oxide, or chloride.

21. The method of claim 1, wherein the inoculum comprises methanol.

22. The method of claim 1, wherein the inoculum comprises a mixture of two or more methylotrophic bacteria strains.

23. The method of claim 1, wherein the inoculum comprises an agriculturally acceptable carrier.

24. The method of claim 23, wherein the agriculturally acceptable carrier comprises a dispersant, a surfactant, an additive, water, a thickener, an anti-caking agent, residue breakdown, a composting formulation, a granular application, diatomaceous earth, an oil, a coloring agent, a stabilizer, a preservative, a polymer, a coating, or a combination thereof.

25. The method of claim 24, wherein the additive comprises an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutant dioate, a benzene acetonitrile derivative, a proteinaceous material, or a combination thereof.

26. The method of claim 25, wherein the proteinaceous material comprises a milk product, wheat flour, soybean meal, blood, albumin, gelatin, or a combination thereof.

27. The method of claim 24, wherein the surfactant comprises a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof.

28. The method of claim 24, wherein the anti-caking agent comprises a sodium salt, a calcium carbonate, a sodium sulfite, a sodium sulfate, diatomaceous earth, or a combination thereof.

29. The method of claim 28, wherein the sodium salt comprises a sodium salt of monomethyl naphthalene sulfonate, a sodium salt of dimethyl naphthalene sulfonate, or a combination thereof.

30. The method of claim 23, wherein the agriculturally acceptable carrier comprises vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

31. The method of claim 1, wherein the inoculum is formulated as a seed coating formulation, a liquid formulation for application to plants or to a plant growth medium, or a solid formulation for application to plants or to a plant growth medium.

32. The method of claim 31, wherein the seed coating formulation is an aqueous or oil-based solution.

33. The method of claim 31, wherein the seed coating formulation is a powder or granular formulation.

34. The method of claim 31, wherein the liquid formulation for application to plants or to a plant growth medium is in a concentrated formulation or a working form formulation.

35. The method of claim 31, wherein the solid formulation for application to plants or to a plant growth medium is a granular formulation or a powder agent.

36. The method of claim 1, wherein the inoculum comprises a fertilizer, a micronutrient fertilizer material, an insecticide, a herbicide, a plant growth amendment, a fungicide, a molluscicide, an algicide, a bacterial inoculant, a fungal inoculant, or a combination thereof.

37. The method of claim 36, wherein the fertilizer comprises a liquid fertilizer.

38. The method of claim 36, wherein the fertilizer comprises ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, or a combination thereof.

39. The method of claim 36, wherein the micronutrient fertilizer material comprises boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof.

40. The method of claim 36, wherein the insecticide comprises an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

41. The method of claim 36, wherein the herbicide comprises a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivative, oxadiazolinone, a phosphate, a phthalate, a picolinic acid compound, a triazine, a triazole, a uracil, a urea derivative, endothall, sodium chlorate, or a combination thereof.

42. The method of claim 36, wherein the fungicide comprises a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

* * * * *